United States Patent
Sitton et al.

(10) Patent No.: US 11,168,352 B2
(45) Date of Patent: Nov. 9, 2021

(54) PROCESS FOR CELL LYSIS AND NUCLEIC ACID AMPLIFICATION

(71) Applicant: 3M INNOVATIVE PROPERTIES COMPANY, St. Paul, MN (US)

(72) Inventors: Gregory W. Sitton, Minneapolis, MN (US); Neil Percy, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 215 days.

(21) Appl. No.: 16/087,750

(22) PCT Filed: Mar. 24, 2017

(86) PCT No.: PCT/US2017/023951
§ 371 (c)(1),
(2) Date: Sep. 24, 2018

(87) PCT Pub. No.: WO2017/176469
PCT Pub. Date: Oct. 12, 2017

(65) Prior Publication Data
US 2019/0112637 A1    Apr. 18, 2019

Related U.S. Application Data

(60) Provisional application No. 62/319,876, filed on Apr. 8, 2016.

(51) Int. Cl.
  C12Q 1/6806  (2018.01)
  C12Q 1/686   (2018.01)
  C12N 1/06    (2006.01)

(52) U.S. Cl.
  CPC ......... *C12Q 1/6806* (2013.01); *C12N 1/06* (2013.01); *C12Q 1/686* (2013.01)

(58) Field of Classification Search
  CPC ................. C12Q 1/6806; C12N 1/06
  See application file for complete search history.

(56) References Cited

U.S. PATENT DOCUMENTS

| | | |
|---|---|---|
| 5,620,869 A | 4/1997 | Woodard et al. |
| 5,726,021 A | 3/1998 | Britschgi et al. |
| 6,218,107 B1 | 4/2001 | Brentano et al. |
| 2012/0003710 A1 | 1/2012 | Leinweber et al. |
| 2014/0038174 A1* | 2/2014 | Fischer ............ C12Q 1/701 435/5 |

FOREIGN PATENT DOCUMENTS

| | | |
|---|---|---|
| JP | 8-149974 | 6/1996 |
| JP | 5006607 | 8/2012 |
| WO | WO 2010/004785 | 1/2010 |
| WO | WO 2013/147043 A | 10/2013 |
| WO | WO 2014/029791 | 2/2014 |
| WO | WO 2014/072366 | 5/2014 |
| WO | WO 2016/036877 | 3/2016 |
| WO | WO 2016/106166 | 6/2016 |
| WO | WO 2016/183012 | 11/2016 |

OTHER PUBLICATIONS

Svec, Direct cell lysis for single-cell gene expression profiling, Front. Oncol., 3:274, pp. 1-11, 2013. (Year: 2013).*
Millipore Sigma, Igepal CA-630, 2020. (Year: 2020).*
Hill, Development of a Nucleic Acid Extraction Procedure for Simultaneous Recovery of DNA and RNA from Diverse Microbes in Water, Pathogens, 4, pp. 335-354, 2015. (Year: 2015).*
Kaneko, Tolerance of loop-mediated isothermal amplification to a culture medium and biological substances, J. Biochem. Biophys. Methods, 70: 499-501, 2007. (Year: 2007).*
Isik et al. 2009. *Bioorganic & Medicinal Chemistry.* 17:158-1163. "Carbonic anhydrase inhibitors: Inhibition of the β-class enzyme from the yeast *Saccharomyces cerevisiae* with sulfonamides and sulfamates".
Lina et al. 1992. *FEMS Microbiology Letters.* 92:133-138. "Comparison of coagulase-negative staphylococci by pulsed-field gel electrophoresis".
Gomez et al. 2013. *Journal of Neuroimmunology.* 261:141-145. "Proteomic analysis of rat tibialis anterior muscles at different stages of experimental autoimmune myasthenia gravis".
Brochure entitled "3M™ Novec™ Fluorosurfactants For Paints and Coatings"; 3M Company; 2009; #98-0212-4164-5; 4 pgs.
Product Information on "3M™ Novec™ Fluorosurfactant FC-4430"; 3M Company; 2011; #98-0212-4160-3; 4 pgs.
Brochure entitled "ProClin® 950 Preservative for Diagnostic Reagents— Directions for Use"; Sigma-Aldrich; #05446-503120; 2009; 1 pg.
Gandelman, O.A. et al.; "Novel Bioluminescent Quantitative Detection of Nucleic Acid Amplification in Real-Time"; PLoS ONE; vol. 5, No. 11; 2010; e14155 (13 pgs).

\* cited by examiner

*Primary Examiner* — Samuel C Woolwine
*Assistant Examiner* — Carolyn L Greene
(74) *Attorney, Agent, or Firm* — Eric E. Silverman (57) ABSTRACT

The present disclosure provides a nucleic acid amplification method. The method comprises forming an enrichment culture by contacting a sample with a nutrient medium having a formulation that does not include a phosphate buffer component; holding the enrichment culture for a period of time at a temperature that facilitates growth of a target microorganism; after holding the enrichment culture, forming an aqueous composition by mixing a first volume of the enrichment culture with a second volume of a lysis buffer; contacting the aqueous composition with an effective amount of a water-insoluble material that sequesters a substance that interferes with a polymerase-mediated nucleic acid amplification reaction; subjecting the aqueous composition to a thermal lysis process; and, after subjecting the aqueous composition to the thermal lysis process, subjecting a portion of the aqueous composition to a nucleic acid amplification process. A composition for a lysis buffer is also disclosed.

12 Claims, 1 Drawing Sheet
Specification includes a Sequence Listing.

PROCESS FOR CELL LYSIS AND NUCLEIC ACID AMPLIFICATION

CROSS REFERENCE TO RELATED APPLICATIONS

This application is a national stage filing under 35 U.S.C. 371 of PCT/US2017/023951, filed Mar. 24, 2017, which claims the benefit of U.S. Provisional Patent Application No. 62/319,876, filed Apr. 8, 2016, the disclosure of which is incorporated by reference in its entirety herein.

This application has associated with it a sequence listing with the file name Sequence_Listing_77512WO003.TXT, created Mar. 9, 2017. The sequence listing file contains 722 bytes and it is incorporated herein by reference in its entirety.

BACKGROUND

Conventional methods for the detection of pathogens and other microorganisms are based on culture methods, but these are time consuming, laborious, and no longer compatible with the needs of quality control and diagnostic laboratories to provide rapid results.

Efforts to overcome difficulties in detecting pathogenic microorganisms (e.g., the long delays involved in culturing the microorganisms) have led to the development of genetic testing such as DNA-based diagnostic methods or nucleic acid proliferation methods. The use of DNA-based methods derives from the premise that each species of pathogen carries unique DNA or RNA signature that differentiates it from other organisms. These techniques are the most promising and are increasingly used for rapid, sensitive and specific detection of microbes.

Advances in biotechnology have led to the development of a diverse array of assays for efficient nucleic acid amplification.

The effective genetic testing of samples containing microorganisms/pathogens requires rapid sensitive assay methods that gives instant or real time results. Time and sensitivity of analysis and inhibition of nucleic acid amplification caused by inhibitory substances in the sample are certain limitations related to the usefulness of genetic testing.

It is desirable to have a composition and a method to efficiently and rapidly reduce or eliminate the inhibition of the nucleic acid amplification of the intended target.

SUMMARY

The present disclosure provides an improved nucleic acid amplification process that eliminates inhibition of the nucleic acid amplification reaction due to inhibitory substances in the sample. Advantageously, the improved method obviates the need to dilute the sample before using it in the nucleic acid amplification reaction, thereby permitting increased sensitivity of the nucleic acid amplification process.

In one aspect, the present disclosure provides a nucleic acid amplification method. The method can comprise forming an enrichment culture by contacting a sample with a nutrient medium that is substantially free of water-soluble phosphate ions, wherein the nutrient medium comprises a first buffer; holding the enrichment culture for a period of time at a temperature that facilitates growth of a target microorganism; after holding the enrichment culture, forming an aqueous composition by mixing a first volume of the enrichment culture with a second volume of a lysis buffer to form a third volume of the aqueous composition, wherein mixing the first volume of the enrichment culture with the second volume of the lysis buffer comprises mixing an undiluted first volume of the enrichment culture with the second volume of the lysis buffer; contacting the aqueous composition with an effective amount of a water-insoluble material that sequesters a substance that interferes with a polymerase-mediated nucleic acid amplification reaction; subjecting the aqueous composition to a thermal lysis process; and after subjecting the aqueous composition to the thermal lysis process, subjecting a portion of the aqueous composition to a nucleic acid amplification process. The lysis buffer is substantially free of water-soluble phosphate ions and comprises a second buffer. The lysis buffer can comprise an organic multivalent cation-chelating reagent, wherein the organic multivalent cation-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45. The lysis buffer can have a pH greater than 8.6 at 25° C. The aqueous composition can have a pH of about 8.45 to 8.85 at 25° C. A combined concentration of the first buffer and the second buffer in the aqueous composition can be at least about 15 mM. A ratio of the first volume to the second volume can be greater than or equal to 3:1 and the ratio of the second volume to the third volume is less than or equal to 1:4.

In another aspect, the present disclosure provides a nucleic acid amplification method. The method can comprise forming an enrichment culture by contacting a sample with a nutrient medium having a formulation that does not include a phosphate buffer component, wherein the nutrient medium comprises a first buffer; holding the enrichment culture for a period of time at a temperature that facilitates growth of a target microorganism; after holding the enrichment culture, forming an aqueous composition by mixing a first volume of the enrichment culture with a second volume of a lysis buffer to form a third volume of the aqueous composition, wherein mixing the first volume of the enrichment culture with the second volume of the lysis buffer comprises mixing an undiluted first volume of the enrichment culture with the second volume of the lysis buffer; contacting the aqueous composition with an effective amount of a water-insoluble material that sequesters a substance that interferes with a polymerase-mediated nucleic acid amplification reaction; subjecting the aqueous composition to a thermal lysis process; and after subjecting the aqueous composition to the thermal lysis process, subjecting a portion of the aqueous composition to a nucleic acid amplification process. The lysis buffer comprises a second buffer. The lysis buffer can comprise an organic multivalent cation-chelating reagent, wherein the organic multivalent cation-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45. The lysis buffer can have a pH greater than 8.6 at 25° C. The aqueous composition can have a pH of about 8.45 to 8.85 at 25° C. A combined concentration of the first buffer and the second buffer in the aqueous composition can be at least about 15 mM. A ratio of the first volume to the second volume can be greater than or equal to 3:1 and the ratio of the second volume to the third volume is less than or equal to 1:4.

In any of the above embodiments, after subjecting the aqueous composition to the thermal lysis process and before subjecting the portion of the aqueous composition to the nucleic acid amplification process, the method further can comprise rehydrating a dehydrated reagent for nucleic acid amplification using the portion of the aqueous composition.

In any of the above embodiments, forming the aqueous composition can consist essentially of mixing the first volume of the enrichment culture with the second volume of the lysis buffer.

In yet another aspect, the present disclosure provides a lysis buffer. The lysis buffer can comprise water, a water-insoluble material that sequesters a substance that interferes with a polymerase-mediated nucleic acid amplification reaction, an organic multivalent cation-chelating reagent, at least one non-ionic surfactant, ferric iron, a reagent for facilitating polymerase activity, and a buffer comprising N-cyclohexyl-3-aminopropanesulfonic acid or a salt thereof. The lysis buffer can comprise less than 1 mM phosphoric acid or a salt thereof. The lysis buffer can have a pH of about 9.8 to 10.5, inclusive, at 25° C.

As used herein, the singular forms "a," "an," and "the" include plural reference unless the context clearly dictates otherwise. The term "and/or" means one or all of the listed elements or a combination of any two or more of the listed elements.

When the term "about" is used in describing a value or an endpoint of a range, the disclosure should be understood to include both the specific value and end-point referred to.

As used herein the terms "comprises", "comprising", "includes", "including", "containing", "characterized by", "having" or any other variation thereof, are intended to cover a non-exclusive inclusion.

The foregoing has outlined some pertinent objects of the disclosure. These objects should be construed to be merely illustrative of some of the more prominent features and applications of the intended disclosure. The disclosure includes other features and advantages which will be described or will become apparent from the following more detailed description of the embodiment.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is to be understood that other embodiments may be utilized and structural or logical changes may be made without departing from the scope of the present disclosure. The present disclosure will now be described more fully herein after. For the purposes of the following detailed description, it is to be understood that the disclosure may assume various alternative variations and step sequences, except where expressly specified to the contrary. Thus, before describing the present disclosure in detail, it is to be understood that this disclosure is not limited to particularly exemplified systems or embodiments that may of course, vary. The use of examples anywhere in this specification including examples of any terms discussed herein is illustrative only, and in no way limits the scope and meaning of the disclosure or of any exemplified term. Likewise, the disclosure is not limited to various embodiments given in this specification.

The present disclosure provides a method for eliminating sample inhibition in a nucleic acid amplification reaction of a sample from a microbial enrichment broth culture. In contrast to conventional methods, the inventive method does not require substantial dilution (i.e., does not require >1:1 dilution) of the enrichment broth immediately prior to the cell lysis step and/or the nucleic acid amplification step. Advantageously, this feature of the method results in an ability to detect lower concentrations of target nucleic acids in the sample.

As used herein, the phrase "nucleic acid," and "nucleic acid sequence," are interchangeable and not intended to be limiting. "Nucleic acid" shall have the meaning known in the art and refers to DNA (e.g., genomic DNA, cDNA, or plasmid DNA), RNA (e.g., mRNA, tRNA, or rRNA), and PNA. It may be in a wide variety of forms, including, without limitation, double-stranded or single-stranded configurations, circular form, plasmids, relatively short oligonucleotides, peptide nucleic acids also called PNA's and the like. The nucleic acid may be genomic DNA, which can include an entire chromosome or a portion of a chromosome. The DNA may include coding (e.g., for coding mRNA, tRNA, and/or rRNA) and/or noncoding sequences (e.g., centromeres, telomeres, intergenic regions, introns, transposons, and/or microsatellite sequences). The nucleic acid may include any of the naturally occurring nucleotides as well as artificial or chemically modified nucleotides, mutated nucleotides, etc. The nucleic acid can include a non-nucleic acid component, e.g., peptides (as in PNA's), labels (radioactive isotopes or fluorescent markers), and the like.

As used herein, "amplifying" and "amplification" refers to a broad range of techniques for increasing polynucleotide sequences, either linearly or exponentially. Exemplary amplification techniques include, but are not limited to, polymerase chain reaction (PCR) or any other method employing a primer extension step. Other non-limiting examples of amplification include, but are not limited to, ligase detection reaction (LDR) and ligase chain reaction (LCR). Amplification methods may comprise thermal-cycling or may be performed isothermally such as Loop mediated isothermal amplification (LAMP-BART). In various embodiments, the term "amplification product" or "amplified product" includes products from any number of cycles of amplification reactions.

As used herein, the "polymerase chain reaction" or PCR is an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence. Each of the above steps may be conducted at a different temperature, preferably using an automated thermocycler.

As used herein, "isothermally amplified" or "isothermal amplification" and like terms refers to a method of amplifying nucleic acid that is conducted at a constant temperature in contrast to amplifications that require cycling between high and low temperatures unlike traditional PCR reactions. This requires that the DNA polymerase is a DNA polymerase having strand displacement activity. Isothermal amplifications are often conducted at substantially a single temperature because primers bind to displaced DNA strands. In isothermal amplifications the reaction mixture comprising the nucleic acid sample and optionally all primers may be heated to a denaturation temperature at which double-stranded nucleic acid in the reaction mixture denatures into single strands (e.g., at least 85° C. to 90° C.) prior to the amplification and optionally prior to addition of the DNA polymerase when the DNA polymerase is inactivated at the denaturation temperature.

As used herein, the terms "intended target", "target nucleic acid region," "target specific nucleic acid," "target region," "target signature sequence" "target nucleic acid(s)", "target nucleic acid sequences," "target" or "target polynucleotide sequence" refers to a nucleic acid of interest.

As used herein, "detecting" or "detection" refers to the disclosure or revelation of the presence or absence in a sample of a target polynucleotide sequence or amplified target polynucleotide sequence product. The detecting can be by end point, real-time, enzymatic, and by resolving the amplification product on a gel and determining whether the expected amplification product is present, or other methods known to one of skill in the art.

As used herein the term "sample" refers to a starting material suspected of containing a nucleic acid. Detecting the nucleic acid in the sample enables one to detect the presence of a target microorganism, for example. Examples of samples include, but are not limited to, food samples (including but not limited to samples from food intended for human or animal consumption such as processed foods, raw food material, produce (e.g., fruit and vegetables), legumes, meats (from livestock animals and/or game animals), fish, sea food, nuts, beverages, drinks, fermentation broths, and/or a selectively enriched food matrix comprising any of the above listed foods), water samples, environmental samples (e.g., soil samples, dirt samples, garbage samples, sewage samples, industrial effluent samples, air samples, or water samples from a variety of water bodies such as lakes, rivers, ponds etc.), air samples (from the environment or from a room or a building), clinical samples, samples obtained from humans suspected of having a disease or condition, veterinary samples, forensic samples, agricultural samples, pharmaceutical samples, biopharmaceutical samples, samples from food processing and manufacturing surfaces, and/or biological samples. Examples for nonfood samples as per the present disclosure may be culture broths. "Culture broth" as used herein refers to a liquid medium for culturing the microorganism.

"Target microorganism", as used herein, refers to a pre-selected microorganism or group of microorganisms, each member of the group of microorganisms having a polynucleotide portion of a genetic element (e.g., a genome or an extra-genomic nucleic acid such as a plasmid) that is identical or substantially identical to other members of the group. In any embodiment, the target microorganism may be a pathogenic microorganism.

Target microorganisms of particular interest include prokaryotic microorganisms (particularly Gram positive bacteria, Gram negative bacteria, and mycoplasma), filamentous fungi, and yeast. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., *Corynebacteria* spp. as well as *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis*, *Streptococcus pneumoniae*, *S. agalactiae*, *S. pyogenes*, *Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracis*, *Pseudomonas aeruginosa*, *Escherichia coli*, *Aspergillus niger*, *A. fumigatus*, *A. clavatus*, *Fusarium solani*, *F. oxysporum*, *F. chlamydosporum*, *Listeria monocytogenes*, *Listeria ivanovii*, *Vibrio cholera*, *V parahemolyticus*, *Salmonella cholerasuis*, *S. typhi*, *S. typhimurium*, *Candida albicans*, *C. glabrata*, *C. krusei*, *Enterobacter sakazakii*, *E. coli* O157 and multiple drug resistant Gram negative rods (MDR).

As used herein, an "inhibitor" means any compound, substance, or composition, or combination thereof, that acts to decrease the activity, precision, or accuracy of an assay, either directly or indirectly, with respect to the activity, precision, or accuracy of the assay when the inhibitor is absent. An inhibitor can be a molecule, an atom, or a combination of molecules or atoms without limitation.

As used herein, the term "inhibitors" refers to inhibitors of enzymes used in amplification reactions, for example. Examples of such inhibitors typically include but not limited to proteins, peptides, lipids, carbohydrates, polyphenols, heme and its degradation products, urea, bile acids, humic acids, polysaccharides, cell membranes, and cytosolic components. The major inhibitors in blood that can affect PCR are hemoglobin, lactoferrin, and IgG, which are present in erythrocytes, leukocytes, and plasma, respectively. Examples of inhibitors also include iron ions or salts thereof, other metal salts such as alkali metal ions, transition metal ions etc., and some indicator dyes present in growth medium.

As used herein, the meaning of "surfactant" is the broadest definition that is readily recognized by a person of ordinary skill in the art. That is, surfactants are wetting agents that lower the surface tension of a liquid and/or lower the interfacial tension between two liquids. A surfactant that does not have a positive or negative charge in water, yet is soluble in water, is a "non-ionic surfactant".

As used herein, "nonionic surfactant" refers to a surfactant molecule whose polar group is not electrically charged. Combinations of two or more non-ionic surfactants are encompassed within the term "non-ionic surfactant". In certain embodiments, one or more surfactants may be used.

As used herein, polyvinylpyrrolidone (PVP) is a water-soluble polymer made from the monomer N-vinylpyrrolidone. Polyvinylpolypyrrolidone (PVPP) is a highly cross-linked modification of PVP. As described herein, polyvinylpyrrolidone, or a modification thereof, can be included in an amplification reaction mixture so as to reduce or eliminate inhibitory substances. A modified PVP includes, but is not limited to polyvinylpolypyrrolidone (PVPP), which is an insoluble highly cross-linked modification of PVP. It will be understood that disclosure herein related to PVP can be adapted to PVPP.

In an embodiment, the composition may comprises a non-ionic polymeric fluorochemical surfactant which belongs to a class of coating additives which provide low surface tensions and exhibits good thermal stability when used in thermal processing applications. A non-ionic polymeric fluorochemical surfactant as per certain embodiments of the present disclosure may be FC-4430 which is 3M™ Novec™ fluorosurfactant.

As used herein the terms "ethylene glycol tetraacetic acid" and "EGTA" refer to ethylene glycol-bis(2-aminoethylether)-N,N,N',N'-tetraacetic acid, a chelating agent. EGTA is a colorless solid which has lower affinity for magnesium, making it more selective for calcium ions. EGTA is useful for making buffer solutions to chelate calcium ions when calcium ions are less concentrated than magnesium, as found in living cells. EGTA is also useful in enzyme assays.

As used herein the term "cell lysis" refers to a process of releasing materials in a cell by disrupting the cell membrane and/or permeablizing the cell envelope such that enzymes and other components of a nucleic acid amplification reaction gain access to the cell's nucleic acids, and in particular, a process of extracting intracellular materials from a cell to isolate DNA or RNA before amplification, such as PCR, LAMP-BART methods and likewise.

According to an embodiment of the present disclosure, cell lysis may be done by thermal methods. The thermal method may be properly selected by those skilled in the art according to the form of cell sample and characteristics of reaction vessel.

As used herein, the term "microorganism" or "microbe" refers to any microscopic organism, which may be a single cell or multicellular organism. The term is generally used to refer to any prokaryotic or eukaryotic microscopic organism capable of growing and reproducing in a suitable culture medium, including without limitation, one or more of bacteria. Microorganisms encompassed by the scope of the present invention includes prokaryotes, namely the bacteria and archaea; and various forms of eukaryotes, comprising the protozoa, fungi, algae and the like. As used herein, the term "culture" or "growth" of microorganisms refers to the method of multiplying microbial organisms by letting them reproduce in predetermined culture media under conditions conducive for their growth. More particularly it is the method of providing a suitable culture medium and conditions to facilitate at least one cell division of a microorganism. Culture media may be solid, semisolid or liquid media containing all of the nutrients and necessary physical growth parameters necessary for microbial growth. The term "target microorganism" refers any microorganism that is desired to be detected.

As used herein, the term "enrichment" refers to the culture method of enriching the growth of a specific microorganism by providing medium and conditions with specific and known attributes that favors the growth of that particular microorganism. The enrichment culture's environment will support the growth of a selected microorganism and, optionally, inhibiting the growth of others.

The use of conventional DNA-based methods is to some extent restricted by the presence of inhibitors. The occurrence of such so called inhibitors, which comprises all substances that have a negative effect on the nucleic acid proliferation reactions, is one of the drawbacks of genetic testing. These inhibitors can originate from the sample itself or may be introduced during sample processing or nucleic acid extraction. The consequence of a partial or total inhibition of the nucleic acid proliferation reactions is a decreased sensitivity or false-negative results, respectively.

Despite the availability of numerous genetic based methods, there is no single rapid, sensitive, inexpensive and less laborious method to efficiently and rapidly reduce or eliminate the inhibition of the nucleic acid amplification of the intended target. To quickly determine the presence of pathogen in targeted sample, there is a need to develop a reliable and accurate assay method which can cater to the increasing need of finding faster, accurate and less time consuming and less laborious assay techniques.

In certain PCR systems an impediment to their ease of use is the inclusion of a protease step. This protease step is used for reducing sample inhibition by digesting food protein (especially red meats) and/or peptones from microbial growth media as well as lysing cells. Surprisingly, it has been found that an aqueous composition formed by a method as per the present disclosure eliminates the need for proteasing a sample. According to a method of the present disclosure, the aqueous composition is contacted with a water-insoluble material (e.g., zirconium oxide particles) that sequesters substances (e.g., polypeptides from the sample and/or from the enrichment medium) in the aqueous composition that interfere with a polymerase-mediated nucleic acid amplification reaction, in combination with an organic multivalent cation-chelating reagent, to neutralize inhibitory proteins. The term "sequester", as used herein, refers to a functional isolation or separation of the interfering substances (i.e., the substances that otherwise interfere with the polymerase-mediated nucleic acid amplification reaction) from an aqueous composition such that the interfering activity of the substances is reduced or eliminated. Advantageously the present disclosure eliminates the step of isolation/purification of the nucleic acid released from lysed cells, which makes the method of the present disclosure faster and simpler.

The present disclosure describes a method of nucleic acid amplification which eliminates the need to protease or otherwise reduce (e.g., via dilution) background protein from the sample. This in turn also leads to the elimination of at least one of the assay steps of the conventional nucleic acid amplification methods. In addition, the method of the present disclosure provides the ability to detect cells (e.g., microorganisms) that are present at a lower concentration than conventional methods (i.e., that require protease treatment or dilution to remove interfering substances) can detect.

The present disclosure generally relates to methods for nucleic acid proliferation of a sample which comprises a cell lysis step and nucleic acid amplification step without an isolation/purification step such as chromatography, centrifugation and likewise in between.

Figure 1:
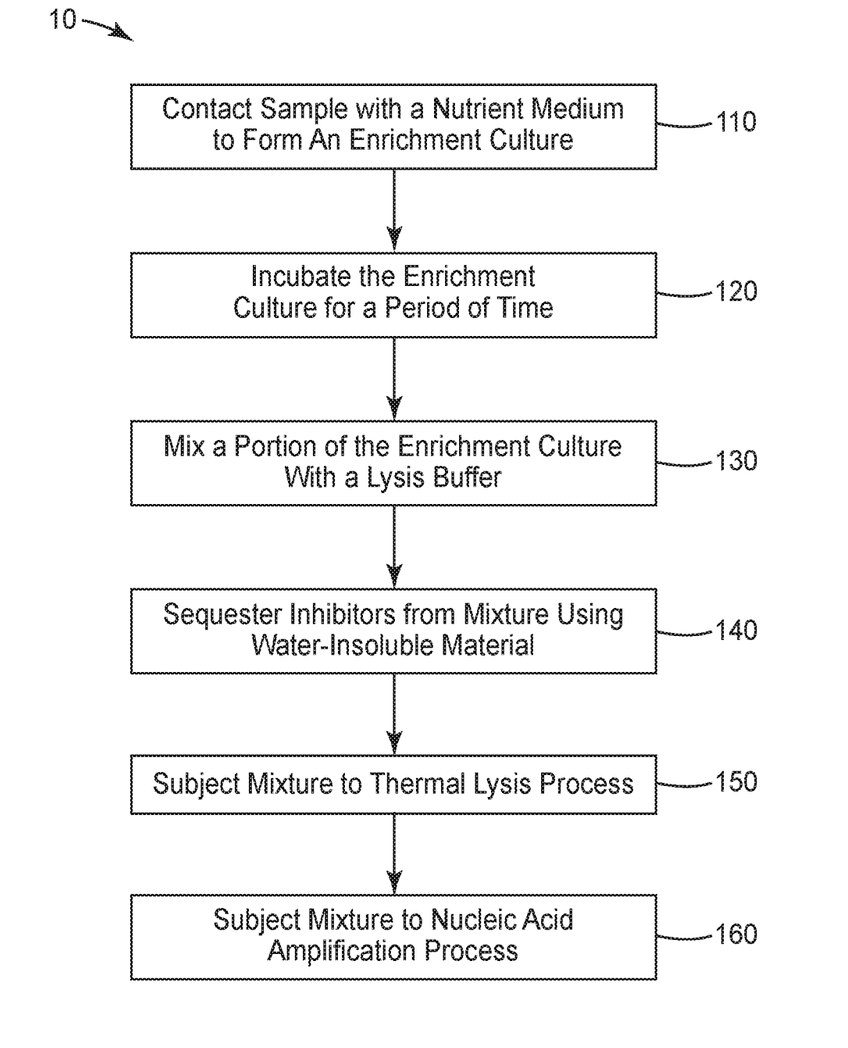
FIG. 1 is a block diagram of one embodiment of a method according to the present disclosure.

The present disclosure provides a method. The method can be used to amplify a nucleic acid present in a sample. In any embodiment, the method can be used to detect a nucleic acid associated with a target microorganism (e.g., a pathogenic microorganism) present in a sample. FIG. 1 is a block diagram showing the one embodiment of a method 10 of amplifying a nucleic acid according to the present disclosure.

The method 10 comprises a step 110 of forming an enrichment culture by contacting a sample with a nutrient medium. The nutrient medium is substantially-free of water-soluble phosphate ions (i.e. inorganic salts of phosphates are not a component of the medium formulation). In addition, the nutrient medium comprises a first buffer. The first buffer is not a nutrient that can be metabolized by the target microorganism to produce biomass or energy.

Samples of particular interest are samples (e.g., processed food samples) that may comprise relatively small numbers of target microorganisms. In any embodiment, the sample (e.g., a carcass rinse, process water, residue from an environmental (e.g., food-processing equipment) swab or sponge) is suspended in an aqueous liquid (e.g., an aqueous nutrient medium for growing target microorganisms).

The nutrient medium facilitates growth of the target microorganism and is substantially free of water-soluble phosphate ions that might interfere with an enzyme-mediated nucleic acid amplification process. In any embodiment, the nutrient medium has a formulation that does not include a phosphate buffer component (e.g., the components of the formulation of the nutrient medium do not include $NaH_2PO_4$, $Na_2HPO_4$, $Na_3PO_4$, $KH_2PO_4$, $K_2HPO_4$ or $K_3PO_4$). The term "formulation", as used herein, refers to a material or mixture prepared according to a particular formula. In addition, the nutrient medium comprises a first buffer. The first buffer is free of or substantially-free of water soluble phosphate ions. The first buffer is present in the nutrient medium at a first concentration (e.g., a least about 5 mM, about 10 mM, about 15 mM, about 20 mM, about 25 mM, about 30 mM, greater than 30 mM). The first buffer can buffer the nutrient medium at a pH (e.g., about 7.0 to about 7.6 at 25° C.) that facilitates growth of the target microorganism.

The nutrient medium can comprise a combination of nutrients known in the art, provided the medium does not include a phosphate ions at a concentration that will inhibit the enzyme-mediated nucleic acid amplification step of the method. For example, Commercially-available ISO buffered peptone water is a nonselective nutrient medium known in the art for pre-enrichment of *Salmonella* and other enteric bacterial species (e.g., *E. coli, Cronobacter* sp.) from food and environmental samples. ISO buffered peptone water comprises peptone, sodium chloride, and a phosphate buffer. The phosphate buffer in commercially-available ISO buffered peptone water is present at a concentration (approximately 35 mM) that inhibits, for example, loop-mediate isothermal nucleic acid amplification. Therefore, a method of detecting *Salmonella* according to the present disclosure could use, for example, a modified buffered peptone water nutrient medium that comprises a phosphate-free first buffer (e.g., a buffer comprising tris(hydroxymethyl)aminomethane ("Tris buffer") or N-cyclohexyl-3-aminopropanesulfonic acid ("CAPS buffer") instead of the phosphate buffer used in the ISO buffered peptone water formulation known in the art. A person having ordinary skill in the art will recognize other phosphate-free buffers (e.g., 3-(N-morpholino)propanesulfonic acid, "MOPS buffer"; 4-(2-hydroxyethyl)-1-piperazineethanesulfonic acid, "HEPES buffer"; 2-[[1,3-dihydroxy-2-(hydroxymethyl)propan-2-yl]amino]ethanesulfonic acid, "TES buffer"; 2-[Bis(2-hydroxyethyl)amino]-2-(hydroxymethyl)propane-1,3-diol, "Bis-tris buffer"; or 3-(cyclohexylamino)-2-hydroxy-1-propanesulfonic acid, "CAPSO buffer") that can be used to buffer the nutrient medium at a pH that is suitable to facilitate growth of a target microorganism.

Referring back to FIG. 1, contacting the sample with the nutrient medium forms an enrichment culture than can be used to propagate target microorganisms that are present in the sample at the time it was contacted with the nutrient medium. Propagating the target microorganisms in the nutrient medium can facilitate detection of the target microorganisms by increasing the number (and concentration) of target microorganisms (and nucleic acid molecules associated therewith) in the nutrient medium.

Thus, the method 10 includes the step 120 of incubating the enrichment culture (i.e., holding the enrichment culture for a period of time at a temperature that facilitates growth of a target microorganism). A person having ordinary skill in the art will recognize suitable temperatures to hold the enrichment culture in order to facilitate growth of the target microorganism. In any embodiment, the enrichment culture can be incubated at a temperature between 25° C. and 44.5° C., inclusive. Many target microorganisms that are pathogenic to humans grow optimally at temperatures between 35-37° C., inclusive.

Holding the enrichment culture for a period of time can comprise holding the enrichment culture for a period of time suitable to permit one or more cell division of a target microorganism, if present, in the enrichment culture. Thus, holding the enrichment culture for a period of time can comprise holding the enrichment culture for about 30 minutes to at least 24 hours. In any embodiment, holding the enrichment culture for a period of time can comprise holding the enrichment culture for about 2 hours to about 18-24 hours. In any embodiment, holding the enrichment culture for a period of time can comprise holding the enrichment culture for about 2 hours to about 6 hours. In any embodiment, holding the enrichment culture for a period of time can comprise holding the enrichment culture for about 2 hours to about 4 hours.

After holding the enrichment culture for a period of time, the method 10 comprises the step 130 of forming an aqueous composition by mixing a first volume of the enrichment culture with a second volume of a lysis buffer to form the aqueous composition (e.g., a third volume of the aqueous composition). In this step, mixing the first volume of the enrichment culture with the second volume of the lysis buffer comprises mixing an undiluted first volume of the enrichment culture with the second volume of the lysis buffer. Thus, if the enrichment culture contains substances that may interfere with a polymerase-mediated nucleic acid amplification reaction, those substances are not diluted prior to mixing the first volume of the enrichment culture with the second volume of the lysis buffer. Advantageously, this feature of the method avoids potentially-unnecessary dilution of the target microorganisms present in the enrichment culture and, thus, provides a greater ability (than methods requiring additional dilution of the enrichment culture) to detect low numbers of target microorganisms in the enrichment culture.

The lysis buffer is an aqueous buffer that comprises a second buffer that works in concert with the first buffer to adjust the pH of the aqueous composition to a pH that is suitable for the enzyme-mediated nucleic acid amplification process. The lysis buffer is free of or substantially-free of water-soluble phosphate ions. In any embodiment, the lysis buffer can have a formulation that does not include a phosphate buffer component (e.g., the components of the formulation of the lysis buffer do not include $NaH_2PO_4$, Na$_2$HPO$_4$, Na$_3$PO$_4$, KH$_2$PO$_4$, K$_2$HPO$_4$ or K$_3$PO$_4$). The term "formulation", as used herein, refers to a material or mixture prepared according to a particular formula. The lysis buffer comprises a second buffer that may comprise a buffer reagent that is identical to the first buffer or it may comprise a buffer reagent that is different from the first buffer. The second buffer is present in the lysis buffer at a second concentration (e.g., at least about 10 mM; about 10 mM, about 20 mM, about 25 mM, about 30 mM, about 40 mM, about 50 mM, greater than 50 mM, about 10 mM to about 50 mM, about 10 mM to about 25 mM, about 25 mM to about 50 mM).

In any embodiment, the lysis buffer has a pH greater than or equal to 8.6 at 25° C., greater than or equal to 9.0 at 25° C., greater than or equal to 9.2 at 25° C., greater than or equal to 9.5 at 25° C., about 8.8 at 25° C., about 9.0 at 25° C., about 9.2 at 25° C., about 9.4 at 25° C., about 9.6 at 25° C., about 9.8 at 25° C., about 8.6-10.0 at 25° C., about 8.6 to 9.8 at 25° C., about 9.0-10.0 at 25° C., or about 9.2-9.8 at 25° C. Thus, when the aqueous composition is formed by mixing the first volume of the enrichment culture with the second volume of the lysis buffer, the aqueous composition has a pH in the range of about 8.45 to about 8.85, inclusive, at 25° C.

The first volume of the enrichment culture is mixed with the second volume of the lysis buffer to form the aqueous composition. Accordingly, the first buffer of the nutrient medium and all components (e.g., the second buffer) of the lysis buffer are present in their respective solutions at concentrations that are selected so that, when the aqueous composition is formed, they are at the proper concentration for the lysis step (described below) and the nucleic acid amplification step (described below).

According to the method of the present disclosure, there exists a first ratio of the first volume of the enrichment culture to the second volume of the lysis solution that are combined to form the third volume of the aqueous composition. In addition, there exists a second ratio of the first volume to the third volume. In any embodiment, the first ratio is greater than or equal to 3:1 and the second ratio is less than or equal to 1:4. In any embodiment, the first ratio is greater than or equal to 4:1 and the second ratio is less than or equal to 1:5. In any embodiment, the first ratio is greater than or equal to 5:1 and the second ratio is less than or equal to 1:6. In any embodiment, the first ratio is greater than or equal to 6:1 and the second ratio is less than or equal to 1:7. In any embodiment, the first ratio is greater than or equal to 7:1 and the second ratio is less than or equal to 1:8. In any embodiment, the first ratio is greater than or equal to 8:1 and the second ratio is less than or equal to 1:9. In any embodiment, the first ratio greater than or equal to 9:1 and the second ratio is less than or equal to 1:10. In any embodiment, the first ratio greater than or equal to 10:1 and the second ratio is less than or equal to 1:11. In any embodiment, the first ratio greater than or equal to 14:1 and the second ratio is less than or equal to 1:15. In any embodiment, the first ratio greater than or equal to 19:1 and the second ratio is less than or equal to 1:20. In any embodiment, the first ratio greater than or equal to 24:1 and the second ratio is less than or equal to 1:25.

Forming the aqueous composition comprises combining the enrichment medium that includes the first buffer and the lysis buffer that includes the second buffer, both as discussed above. In any embodiment, forming the aqueous composition consists essentially of mixing the first volume of the enrichment culture with the second volume of the lysis buffer.

When the aqueous composition is formed, it has a combined buffer concentration that equals the sum of the moles of the first and second buffers divided by the volume of the aqueous composition. In any embodiment, the combined buffer concentration in the aqueous composition is greater than or equal to 15 mM. In any embodiment, the combined buffer concentration in the aqueous composition is greater than or equal to 20 mM. In any embodiment, the combined buffer concentration in the aqueous composition is greater than or equal to 25 mM. In any embodiment, the combined buffer concentration in the aqueous composition is greater than or equal to 30 mM. In any embodiment, the combined buffer concentration in the aqueous composition is greater than or equal to 40 mM. In any embodiment, the combined buffer concentration in the aqueous composition is greater than or equal to 50 mM. In any embodiment, the combined buffer concentration in the aqueous composition is about 15 mM to about 50 mM, inclusive. In any embodiment, the combined buffer concentration in the aqueous composition is about 15 mM to about 25 mM, inclusive.

Returning to FIG. 1, the method 10 includes the step 140 of contacting the aqueous composition with an effective amount of a water-insoluble material that sequesters a substance that interferes with a polymerase-mediated nucleic acid amplification reaction. Advantageously, this sequestration obviates the need for a dilution step (i.e., to reduce the concentration of the interfering substance in the sample) prior to the cell lysis step and/or nucleic acid amplification of the method. In any embodiment, the water-insoluble material can comprise particles. Suitable particles include, for example, zirconium oxide particles hydroxyapatite particles and mixtures thereof. In any embodiment, the water-insoluble material can be suspended and/or dispersed in the lysis buffer. Thus, in any embodiment, forming the aqueous composition comprises forming an aqueous composition that comprises the water-insoluble material.

In any embodiment, the water-insoluble material (e.g., zirconium oxide particles and/or hydroxyapatite particles) may comprise nanoparticles (e.g., the zirconium oxide particles or hydroxyapatite particles have a median particle size that is about 100 nm to less than 1.0 μm). In any embodiment, the zirconium oxide particles or hydroxyapatite particles can have a mean particle size of about 100 nm to about 200 nm. In any embodiment, the zirconium oxide particles or hydroxyapatite particles can have a mean particle size of about 100 nm to about 250 nm. In any embodiment, the zirconium oxide particles or hydroxyapatite particles can have a mean particle size of about 100 nm to about 500 nm. These nanoparticles can exist in a stable dispersion in the aqueous composition at the pH indicated above by the inclusion of citrate in the aqueous composition, as disclosed herein.

A dispersion of nanoparticles (e.g., zirconium oxide nanoparticles or hydroxyapatite nanoparticles) may be characterized by its surface area per unit volume. In any embodiment, after formation of the composition of the present disclosure, the aqueous composition may comprise nanoparticles having a surface area of at least 10 m$^2$/L. In any embodiment, the aqueous composition of the present disclosure may comprise nanoparticles having a surface area of about 10 m$^2$/L to about 600 m$^2$/L, inclusive. In any embodiment, the aqueous composition of the present disclosure may comprise nanoparticles having a surface area of at least about 25 m$^2$/L to about 600 m$^2$/L. In any embodiment, the aqueous composition of the present disclosure may comprise nanoparticles having a surface area of at least about 50 m$^2$/L to about 600 m$^2$/L. In any embodiment, the aqueous composition of the present disclosure may comprise nanoparticles having a surface area of at least about 100 m²/L to about 600 m²/L. In any embodiment, the aqueous composition of the present disclosure may comprise nanoparticles having a surface area of at least about 200 m²/L to about 600 m²/L. In any embodiment, the aqueous composition of the present disclosure may comprise nanoparticles having a surface area of at least about 300 m²/L to about 600 m²/L. In any embodiment, the aqueous composition of the present disclosure may comprise nanoparticles having a surface area of at least about 400 m²/L to about 600 m²/L. In any embodiment, the aqueous composition of the present disclosure may comprise nanoparticles having a surface area of about 600 m²/L.

Aqueous compositions of the present disclosure comprising zirconium oxide nanoparticles can be stabilized such that the particles substantially remain in suspension for extended periods of time (e.g., months, and/or years) and/or are resuspended with minimal effort. This can be accomplished by adding a dispersion stabilizer to the composition. The stabilizer can be provided, for example, in the lysis buffer, as discussed herein. A particularly-preferred dispersion stabilizer that can be used in an aqueous composition of the present disclosure includes a polycarboxylic acid compound such as 2-hydroxypropane-1,2,3-tricarboxylic acid (citric acid) or salts thereof, such as potassium citrate, ferric ammonium citrate, for example.

Thus, in any embodiment of a method of the present disclosure, forming the aqueous composition by mixing the first volume of the enrichment culture with the second volume of the lysis buffer comprises forming the aqueous composition with the water-insoluble material that sequesters a substance that interferes with a polymerase-mediated nucleic acid amplification reaction.

An aqueous composition formed by the method of the present disclosure further can comprise an organic multivalent cation-chelating reagent. The organic multivalent cation-chelating reagent can be provided in the lysis buffer at a concentration that, when diluted into the enrichment medium to form the aqueous composition, is effective to chelate ferric iron ions that may otherwise inhibit a nucleic acid amplification reaction.

The organic multivalent cation-chelating reagent has a predefined affinity constant for ferric ($Fe^{+3}$) iron ions. In deionized water at pH 8.45 and 20° C., the organic multivalent cation-chelating reagent has an affinity constant greater than or equal to $10^{4.2}$ with respect to ferric iron ions. The organic multivalent cation-chelating reagent also has a predefined affinity constant for magnesium ($Mg^{+2}$) ions. In deionized water at pH 8.45 and 20° C., the organic multivalent cation-chelating reagent has an affinity constant less than $10^{3.8}$ with respect to magnesium ions. Thus, in the aqueous composition of the present disclosure at pH 8.45, the organic multivalent cation-chelating reagent has a higher affinity for ferric iron ions than for magnesium ions.

Suitable multivalent cation-chelating reagents include organic molecules. In any embodiment, the organic multivalent cation-chelating reagent is water-soluble. In any embodiment, the organic multivalent cation-chelating reagent comprises a plurality of carboxylate groups. Non-limiting examples of suitable organic multivalent cation-chelating reagents include ethylene glycol-bis(2-aminoethylether)-N,N,N',N'-tetraacetic acid (EGTA); N,N,N',N'-tetrakis(2-pyridylmethyl)ethane-1,2-diamine (TPEN); 1,2-bis(o-aminophenoxy)ethane-N,N,N',N'-tetraacetic acid (BAPTA); N-(2-hydroxyethyl) ethylenediamine-N,N',N'-tetraacetic acid (HEDTA); and salts thereof.

An aqueous composition formed by the method of the present disclosure further can comprise ferric iron. The organic multivalent cation-chelating reagent can be provided in the lysis buffer. Accordingly, an aqueous composition of the present disclosure may comprise ferric iron ions. In any embodiment, the ferric iron can be provided in the composition by ferric ammonium citrate. Thus, the composition may further comprise citrate ions. Advantageously, the citrate ions may facilitate and/or stabilize dispersion of the water-insoluble material (e.g., particles) in aqueous compositions formed in a method of the present disclosure.

In any embodiment, ferric iron can be present in the aqueous composition formed in a method according to the present disclosure at a concentration of ferric ions (i.e., dissolved ferric iron) of about 55 µM-385 µM. In any embodiment, the ferric iron can be provided in the lysis buffer, for example. In certain embodiments the concentration of ferric ions may be at least 110 µM, in certain other embodiments it may be at least 165 µM. In other embodiments the concentration of ferric ions may be at least 220 µM, and in other embodiments it may be at least 275 µM or at least 330 µM. According to the present disclosure, in an aqueous composition wherein the organic multivalent cation-chelating reagent comprises EGTA, the aqueous composition has a molar ratio of dissolved ferric iron/EGTA of about 0.04 to about 0.28. In certain preferred embodiments, the aqueous composition has a molar ratio of dissolved ferric iron/EGTA of about 0.14 to about 0.18.

In any embodiment of a method according to the present disclosure, ferric iron (e.g., provided as ferric ammonium citrate) is present in the aqueous composition at a concentration of ferric ions of about 50 µM-350 µM. Thus, the concentration of ferric iron in the lysis buffer is selected so that, when mixed with the enrichment medium, it provides the aforementioned concentration of ferric ions in the aqueous composition. In certain embodiments the concentration of ferric ions in the aqueous composition may be at least 100 µM, in certain other embodiments it may be at least 150 µM. In other embodiments the concentration of ferric ions may be at least 200 µM, and in other embodiments it may be at least 250 µM or at least 300 µM. According to the present disclosure, in an aqueous composition wherein the organic multivalent cation-chelating reagent comprises EGTA, the aqueous composition, when formed, has a molar ratio of $Fe^{3+}$/EGTA of about 0.04 to about 0.28. In certain preferred embodiments, the aqueous composition, when formed, has a molar ratio of $Fe^{3+}$/EGTA of about 0.14 to about 0.18.

An aqueous composition formed by the method of the present disclosure further can comprise a reagent for facilitating polymerase activity such as, for example, magnesium sulfate heptahydrate. The reagent for facilitating polymerase activity can be provided in the lysis buffer at a concentration that, when diluted into the enrichment medium to form the aqueous composition, is effective to facilitate polymerase activity in a nucleic acid amplification reaction.

In any embodiment of a method according to the present disclosure, the aqueous composition comprises at least one non-ionic surfactant. In any embodiment, the non-ionic surfactant can be provided in the lysis buffer. Accordingly, the aqueous composition, when formed, may comprise one or more of any non-ionic surfactant. Preferably, the non-ionic surfactant has a Hydrophilic-lipophilic balance of about 11 to about 16. Surfactants with a Hydrophilic-lipophilic balance in this range permit sufficient activity of the DNA polymerases in PCR and LAMP nucleic acid amplification reactions as well as permit sufficient luciferase and ATP sulphurlyase activity in the BART reporter technology. Examples of suitable non-ionic surfactants include, but are not limited to TRITON™ series of detergents, including, but not necessarily limited to, TRITON X-100 (t-octylphenoxypolyethoxyethanol) and its derivatives, TRITON X-114, TRITON X-405, TRITON X-101, TRITON N-42, TRITON N-57, TRITON N-60, TRITON X-15, TRITON X-35, TRITON X-45, TRITON X-102, TRITON X-155, TRITON X-165, TRITON X-207, TRITON X-305, TRITON X-705-70 and TRITON B-1956; sorbitan fatty acid ester, Polyoxyethylene (POE)sorbitan fatty acid ester (e.g., Tween), POE alkyl ether (e.g., Brij), nonylphenol, lauryl alcohol, polyethylene glycol, polyoxyethylene-polyoxypropylene block polymer, POE alkyl amine, and POE fatty acid bisphenyl ether and fluorosurfactants such as 3M Novec™ engineered liquid surfactants FC-4430 and FC4432, and Dow chemical FS series fluorosurfactants, for example.

In any embodiment of the aqueous composition formed by a method according to the present disclosure, the concentration of such a non-ionic surfactant in the aqueous composition is not particularly limited, as long as the beneficial effects of the present invention (i.e., with respect to facilitation of nucleic acid amplification) can be achieved. In any embodiment, the aqueous composition formed by a method of the present disclosure comprises about 0.005% (w/v) to about 0.3% (w/v) surfactant. Accordingly, in any embodiment, the aqueous composition comprises up to about 0.3% (w/v) surfactant. In certain embodiments the concentration of surfactant may be at least 0.01% (w/v) and in certain other embodiments it may be at least 0.025% (w/v) and in another embodiment it is 0.032% (w/v).

Optionally, in any embodiment of a method of the present disclosure, the aqueous composition, when formed comprises PVP with a nominal molecular weight of 30 KDa to 1.3 MDa. The PVP can be provided in the lysis buffer. In one aspect of the disclosure, PVP has a nominal molecular weight of 360 KDa.

In an embodiment of a method of the present disclosure, PVP may be included in the aqueous composition when low amounts of the non-ionic surfactant is used. In any embodiment, the PVP can be provided in the lysis buffer, for example. Advantageously, the PVP can sequester inhibitors (e.g., polyphenols) and thereby prevent them from interfering with a nucleic acid amplification assay. In an embodiment, the aqueous composition, when formed, comprises 0% w/v up to about 0.043% w/v PVP. When the nonionic surfactant is present in the composition at a concentration of 0.005% to 0.01% w/v, the composition may comprise about 0.01% w/v to about 0.043% w/v PVP. Each of the above concentrations apply also to a modified PVP.

In certain embodiments of the disclosure (e.g., when the nonionic surfactant concentration is >0.01% w/v in the aqueous composition), PVP may not be included in the aqueous composition. Check to see that PVP can be provided in the lysis buffer.

In any embodiment of a method according to the present disclosure, the organic multivalent cation-chelating reagent, when present in the aqueous composition, comprises EGTA. In any embodiment, the organic multivalent cation-chelating reagent can be provided to the composition in the form of a salt. In certain embodiments, the composition may include, for example, a sodium salt of EGTA. In another embodiment of the present disclosure, the aqueous composition may include, for example, a potassium salt of EGTA.

In any embodiment of a method of the present disclosure, the aqueous composition, when formed, may comprise $Fe^{3+}$ (e.g., provided in the lysis buffer as ferric ammonium citrate) and ethylene glycol tetraacetic acid (e.g., provided in the lysis buffer as a salt (e.g., a monovalent cation salt) of ethylene glycol tetraacetic acid). Thus, in the aqueous composition, there can exist a molar ratio of ethylene glycol tetraacetic acid and $Fe^{3+}$. In any embodiment, the molar ratio of ethylene glycol tetraacetic acid to $Fe^{3+}$ in the aqueous composition is about 0.04 to about 0.28.

In any embodiment of a method according to the present disclosure, the aqueous composition, when, may comprise EGTA at a concentration of 0.5 mM to 5 mM. In any embodiment, the EGTA can be provided in the lysis buffer, for example.

In any embodiment of a method according to the present disclosure, the aqueous composition, when formed, optionally can comprise magnesium or salts thereof and/or potassium or salts thereof. Accordingly, the aqueous composition can comprise magnesium or potassium ions. These can be provided in the lysis buffer, for example. They may be present in the aqueous composition to facilitate the nucleic acid amplification reaction (e.g., PCR (e.g., qPCR), LAMP) that follows the sample preparation step. In any embodiment, the aqueous composition according to the present disclosure can comprise about 1 mM to about 15 mM magnesium ions and/or about 5 mM to about 500 mM potassium ions. In any embodiment, the aqueous composition can comprise about 20 mM to about 60 mM potassium ions. The magnesium or potassium ions can be provided in the lysis buffer, for example.

In any embodiment of a method according to the present disclosure, the aqueous composition, when formed, optionally can comprise an indicator dye to monitor the approximate temperature of an aqueous solution comprising the composition. The indicator dye can be provided in the lysis buffer, for example. Advantageously, the indicator dye can provide a first visual indication (e.g., a first observable color) to indicate that an aqueous mixture comprising the composition has reached a temperature (e.g., about 100° C.) approximately in a range that is suitable for thermal lysis of microbial cells in contact with the composition In addition, the indicator dye can provide a second visual indication (e.g., a second color) to indicate that the aqueous mixture comprising the composition has cooled to a temperature (e.g., ≤45° C.) that is suitable to remove a portion of the mixture and place it into a nucleic acid amplification reaction. Certain pH indicators (e.g., those having a transition range that at least partially extends between a pH of about 8.8 and about 7.2) can be readily monitored as the pH of the aqueous mixture changes during heating and cooling steps.

Suitable visible dyes include, for example, Cresol Red, which has a reddish-purple color when pH is higher than 8.8 and a yellow color when pH is less than 7.2. Thus, in any of the embodiment of a method of the present disclosure, the indicator dye may be cresol red.

Returning to FIG. 1, the method 10 comprises the step 150 of subjecting the aqueous composition to a thermal lysis process. Thermal lysis processes are generally known in the art and are used in nucleic acid amplification methods to disrupt cells, if present in the sample, so that the nucleic acid present in the cells is accessible to the components (e.g., polymerase, primers, dNTP's) of the amplification reaction. In general, the aqueous composition of the method of the present disclosure is disposed in a vessel (e.g., a reaction tube, a multiwell plate) that is contacted with a heat source (e.g., a heat block, a water bath, an oil bath) that heats the contents of the vessel (i.e., the aqueous composition) to a predefined temperature of about 95° C. to about 102° C., inclusive, for a period of time (e.g., about 5 minutes to about 30 minutes, inclusive). After the period of time, the vessel is removed from contact with the heat source and allowed to cool (e.g., to a temperature less than or equal to 45° C.).

After subjecting the aqueous composition to the thermal lysis process, the method 10 comprises the step 160 of subjecting a portion of the aqueous composition to a nucleic acid amplification process. The nucleic acid amplification process optionally includes real-time detection of the amplification reaction. For example, the portion of the aqueous composition may be subjected to nucleic acid amplification by LAMP-BART using appropriate oligonucleotide primers that are specific to one or more microbe nucleic acid sequences (e.g., unique nucleic acid sequences) that indicate a presence of the target microorganism in the sample. Additionally or alternatively, amplification products may then be further subjected to testing with specific probes (or reporter probes) to allow detection of microbial nucleic acid sequences that have been amplified from the sample. In some embodiments, if a microbial nucleic acid sequence is amplified from a sample, further analysis may be performed on the amplification product to further identify, quantify and analyze the detected the microbe (e.g., to determine parameters such as, but not limited to, the microbial species or strain, pathogenicity, quantity etc.).

The nucleic acid amplification methods used in a method according to the present disclosure may be performed isothermally or by using a thermocycling process (e.g., polymerase chain reaction (PCR). Isothermal techniques include but not limited loop-mediated isothermal amplification (LAMP), strand displacement amplification (SDA), nucleic acid sequence-based amplification (NASBA). The reaction proceeds at a constant temperature using strand displacement reactions. Amplification can be completed in a single step, for example, by incubating the portion of the aqueous composition with primers, a DNA polymerase with strand displacement activity, and deoxyribonucleotide triphosphates at a constant temperature. In addition to steps or reactions that increase the number of copies of a target nucleic acid sequence, the amplification methods optionally may include steps or reactions to detect the amplified target nucleic acid sequence. Such detection steps or reactions are well known to a person having ordinary skill in the art and include, for example, bioluminescent real-time reporter (BART) steps or reactions.

In an embodiment of the present disclosure, the isothermal amplification reaction is a Loop-mediated isothermal amplification (LAMP-BART) method. LAMP can amplify DNA with high specificity, efficiency and rapidity under isothermal condition. The LAMP method can include the use of a Bst DNA polymerase and set of four to six specific designed primers that recognize a total of six distinct sequences of the target DNA and with strand displacement activity. In Loop-mediated isothermal amplification (LAMP), target-specific amplification is achieved by the use of 4 to 6 different primers specifically designed to recognize 6 to 8 distinct regions on the target gene, respectively. Such methods typically amplify nucleic acid copies $10^9$-$10^{10}$ times in 15-60 minutes. In addition, the presence of, for example, ATP-sulfurylase, adenosine-5'-O-persulfate, luciferin, and luciferase in the amplification reaction permits detection of a LAMP-mediated amplification reaction via bioluminescence (i.e., the BART reaction).

In addition to the primers, LAMP-BART techniques use Tris, sulfate compounds (such as $MgSO_4$, $NH_4SO_4$) and potassium chloride to maintain enzyme functionality. Thus, such compounds act as enhancers to facilitate the LAMP-BART coupled reaction. Tris is an organic compound (more formally known as tris (hydroxymethyl) aminomethane, with the formula $(HOCH_2)_3CNH_2$). Strand displacement techniques, such as LAMP, use Tris as a buffer, which maintains the reaction at an optimal pH for the reactions to occur.

Using LAMP, the target nucleic acid sequence is amplified at a constant temperature of 60° C. to 65° C. using either two or three pairs of primers and a polymerase with high strand displacement activity in addition to a replication activity. The loop-mediated isothermal amplification (LAMP) reaction is a highly specific, sensitive, isothermal nucleic acid amplification reaction. LAMP employs a set of four primers, termed forward inner primer (FIP), backward inner primer (BIP), forward displacement primer (F3) and backward displacement primer (B3). These four different primers are used to identify 6 distinct regions on the target gene, which adds highly to the specificity. Due to the specific nature of the action of these primers, the amount of DNA produced in LAMP is considerably higher than PCR-based amplification. Furthermore, two optional primers can be included which effectively accelerate the reaction; these are termed forward loop primer (LF) and backward loop primer (LB). The inner primers (FIP and BIP) contain sequences of the sense and antisense strands of the target DNA, while the displacement primers (F3 and B3) and the loop primers (LF and LB) each contain a single target sequence. In total, eight target sequences are recognized when including loop primers (LF and LB) in the reaction. A DNA polymerase is used to amplify the target sequence of interest. Many different DNA polymerases may be used including engineered DNA polymerases not found in nature, the most common being the Bst DNA polymerase while the *Geobacillus* sp. large fragment (GspSSD) DNA polymerase is used less often.

The LAMP reaction is initiated by DNA synthesis primed by the inner primers (FIP and BIP). This is followed by DNA synthesis primed by a displacement primer (F3 or B3) which releases a single-stranded DNA. This single-stranded DNA serves as template for DNA synthesis primed by the second inner and displacement primers that hybridize to the other end of the target. This produces a stem-loop DNA structure. In subsequent LAMP cycling, one inner primer hybridizes to the loop on the product and initiates displacement DNA synthesis. This yields the original stem-loop DNA and a new stem-loop DNA with a stem twice as long. The cycling reaction continues with accumulation of around $10^9$ copies of target in less than an hour. The inclusion of one or two loop primers (LF and/or LB) accelerates the LAMP reaction by hybridizing to the stem-loops, except for the loops that are hybridized by the inner primers, and prime strand displacement DNA synthesis. A variety of LAMP amplification detection methods exist. Non-specific target detection may be obtained through visual identification of a turbid sample as magnesium pyrophosphate precipitates in a positive LAMP reaction. For better visibility of a positive reaction, various agents, such as hydroxy naphthol blue or calcein, may be added to the reaction. Alternatively, fluorescent detection may be achieved using a DNA intercalating dye, such as cresol red, SYBR green, Picogreen or propidium iodide, which is added to the reaction reagent or added after the completion of the reaction for end point analysis.

In any embodiment, subjecting a portion of the aqueous composition to a nucleic acid amplification process comprises contacting a the portion of the aqueous composition with components of an isothermal nucleic acid amplification reaction for a target nucleic acid species (e.g. a target nucleic acid species associated with a target microorganism), thereby providing an amplification reaction mixture; incubating the amplification reaction mixture under conditions sufficient for the nucleic acid amplification reaction to proceed, thereby providing a product; and determining whether an indicator of the target nucleic acid species is present in the product.

The components of the amplification reaction may be provided in a solution and/or in dried (e.g., lyophilized) form. When one or more of the components are provided in dried form, a resuspension or reconstitution buffer may be also be used. Alternatively, after forming the aqueous mixture comprising the sample and, after subjecting the aqueous mixture to a thermal lysis procedure, the aqueous mixture can be used to reconstitute the components of the isothermal reaction.

Based on the particular type of amplification reaction, the reaction mixture can contain buffers, salts, nucleotides, and other components as necessary for the reaction to proceed. The reaction mixture may be incubated at a specific temperature appropriate to the reaction.

In another aspect, the present disclosure provides an aqueous lysis buffer. The lysis buffer, when combined with a predetermined volume of aqueous sample, provides a component that facilitate lysis of microorganism cells, a component that sequester substances that would otherwise interfere with a nucleic acid amplification reaction, and a component that facilitates a nucleic acid amplification reaction. Thus, in another aspect, the present disclosure provides a lysis buffer.

The aqueous lysis buffer includes (e.g., dispersed and/or suspended) therein a water-insoluble material (e.g., zirconium oxide or hydroxyapatite particles) that sequesters a substance that interferes with a polymerase-mediated nucleic acid amplification reaction, as described herein; an organic multivalent cation-chelating reagent (e.g., EGTA), as described herein; at least one non-ionic surfactant (e.g., TRITON™ X-100 detergent), as described herein; ferric iron (e.g., ferric ammonium citrate), as described herein; a reagent for facilitating polymerase activity (e.g., magnesium sulfate heptahydrate), as described hereinabove, and a buffer (e.g., CAPS buffer) that substantially free of phosphate, as described hereinabove. Preferably, the lysis buffer is substantially free of phosphate. However, because the lysis buffer is provided as a concentrate that is intended to be diluted (e.g., 1:3, 1:4, 1:5, 1:10, 1:20, 1:25, 1:30) into the aqueous sample, the lysis buffer may comprise detectable amounts of phosphate (e.g., ≤10 mM, ≤5 mM, ≤2 mM, ≤1 mM, ≤0.5 mM, ≤0.2 mM, ≤0.1 mM, or ≤0.01 mM of the composition comprises a salt of phosphoric acid). The lysis buffer has a pH greater than or equal to 8.6 at 20°, greater than or equal to 9.0 at 25° C., greater than or equal to 9.2 at 25° C., greater than or equal to 9.5 at 25° C., greater than or equal to about 9.8 at 25° C., greater than or equal to about 9.9 at 25° C., about 8.8 at 25° C., about 9.0 at 25° C., about 9.2 at 25° C., about 9.3 at 25° C., about 9.4 at 25° C., about 9.6 at 25° C., about 9.8 at 25° C., about 9.9 at 25° C., about 10.0 at 25° C., about 10.1 at 25° C., about 10.2 at 25° C., about 10.3 at 25° C., about 10.5 at 25° C., about 8.6-10.0 at 25° C., about 8.6 to 9.8 at 25° C., about 9.0-10.5 at 25° C., about 9.3-10.5 at 25° C., about 9.8-10.5 at 25° C., about 9.9-10.5 at 25° C., or about 9.2-9.8 at 25° C., as described hereinabove.

Optionally, the lysis buffer can comprise polyvinylpyrrolidone (PVP) or polyvinylpolypyrrolidone (PVPP), as described herein; a reagent (e.g., ammonium sulfate, potassium chloride) to facilitate polymerase-mediated nucleic acid amplification, as described herein; a reagent (e.g., citric acid or a salt thereof) to facilitate nanoparticle dispersion, as described herein; an indicator dye (e.g., cresol red), as described herein; a preservative (e.g., PROCLIN® 950 biocide), as described herein; or a combination of any two or more of the foregoing optional components.

Table 1 in the Example section shows a formulation for one embodiment of a composition for a lysis buffer according to the present disclosure. The concentrations listed in Table 1 are selected for use in a method wherein one part of the lysis buffer is mixed with 10 parts of an aqueous sample (as described in Example 1), resulting in a mixture that has the appropriate final concentration of each component in order to facilitate thermal lysis and nucleic acid amplification (e.g., using a LAMP-BART amplification technique). A person having ordinary skill in the art will recognize that the concentrations of each component of the lysis buffer may be varied according to the desired ratio of lysis buffer:sample in order to achieve the proper final concentration of each component in any given protocol.

Exemplary Embodiments

Embodiment A is a nucleic acid amplification method, said method comprising:

forming an enrichment culture by contacting a sample with a nutrient medium that is substantially free of water-soluble phosphate ions, wherein the nutrient medium comprises a first buffer;

holding the enrichment culture for a period of time at a temperature that facilitates growth of a target microorganism;

after holding the enrichment culture, forming an aqueous composition by mixing a first volume of the enrichment culture with a second volume of a lysis buffer to form a third volume of the aqueous composition;

wherein mixing the first volume of the enrichment culture with the second volume of the lysis buffer comprises mixing an undiluted first volume of the enrichment culture with the second volume of the lysis buffer;

wherein the lysis buffer is substantially free of water-soluble phosphate ions and comprises a second buffer;

wherein the lysis buffer comprises an organic multivalent cation-chelating reagent, wherein the organic multivalent cation-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45;

wherein the lysis buffer has a pH greater than 8.6 at 25° C.;

wherein the aqueous composition has a pH of about 8.45 to 8.85 at 25° C.;

wherein a combined concentration of the first buffer and the second buffer in the aqueous composition is at least about 15 mM;

wherein a ratio of the first volume to the second volume is greater than or equal to 3:1 and the ratio of the second volume to the third volume is less than or equal to 1:4;

contacting the aqueous composition with an effective amount of a water-insoluble material that sequesters a substance that interferes with a polymerase-mediated nucleic acid amplification reaction;

subjecting the aqueous composition to a thermal lysis process; and after subjecting the aqueous composition to the thermal lysis process, subjecting a portion of the aqueous composition to a nucleic acid amplification process.

Embodiment B is a nucleic acid amplification method, said method comprising:

forming an enrichment culture by contacting a sample with a nutrient medium having a formulation that does not include a phosphate buffer component, wherein the nutrient medium comprises a first buffer;

holding the enrichment culture for a period of time at a temperature that facilitates growth of a target microorganism;

after holding the enrichment culture, forming an aqueous composition by mixing a first volume of the enrichment culture with a second volume of a lysis buffer to form a third volume of the aqueous composition;

wherein mixing the first volume of the enrichment culture with the second volume of the lysis buffer comprises mixing an undiluted first volume of the enrichment culture with the second volume of the lysis buffer;

wherein the lysis buffer comprises a second buffer;

wherein the lysis buffer comprises an organic multivalent cation-chelating reagent, wherein the organic multivalent cation-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45;

wherein the lysis buffer has a pH greater than 8.6 at 25° C.;

wherein the aqueous composition has a pH of about 8.45 to 8.85 at 25° C.;

wherein a combined concentration of the first buffer and the second buffer in the aqueous composition is at least about 15 mM;

wherein a ratio of the first volume to the second volume is greater than or equal to 3:1 and the ratio of the second volume to the third volume is less than or equal to 1:4;

contacting the aqueous composition with an effective amount of a water-insoluble material that sequesters a substance that interferes with a polymerase-mediated nucleic acid amplification reaction;

subjecting the aqueous composition to a thermal lysis process; and after subjecting the aqueous composition to the thermal lysis process, subjecting a portion of the aqueous composition to a nucleic acid amplification process.

Embodiment C is the method of Embodiment A or Embodiment B, wherein the components of the formulation of the nutrient medium do not include $NaH_2PO_4$, $Na_2HPO_4$, $Na_3PO_4$, $KH_2PO_4$, $K_2HPO_4$ or $K_3PO_4$.

Embodiment D is the method of any one of the preceding Embodiments, wherein the components of the formulation of the nutrient medium do not include $NaH_2PO_4$, $Na_2HPO_4$, $Na_3PO_4$, $KH_2PO_4$, $K_2HPO_4$ or $K_3PO_4$.

Embodiment E is the method of any one of the preceding Embodiments, wherein the lysis buffer further comprises ferric iron.

Embodiment F is the method of any one of the preceding Embodiments, wherein the lysis buffer further comprises a reagent selected from the group consisting of a nanoparticle dispersion stabilizer, a non-ionic surfactant having a Hydrophilic-lipophilic balance of about 11 to about 16, polyvinylpyrrolidone, magnesium sulfate heptahydrate, a fluorosurfactant, an indicator dye, and a combination of any two or more of the foregoing reagents.

Embodiment G is the method of any one of the preceding Embodiments, wherein holding the enrichment culture for a period of time comprises holding the enrichment culture for a period of about 4 hours to about 24 hours.

Embodiment H is the method of any one of the preceding Embodiments, wherein the ratio of the first volume to the second volume is greater than or equal to 5:1 and the ratio of the second volume to the third volume is less than or equal to 1:6.

Embodiment I is the method of any one of the preceding Embodiments, wherein forming the aqueous composition by mixing the first volume of the enrichment culture with the second volume of the lysis buffer comprises forming the aqueous composition with the plurality of zirconium oxide particles disposed therein.

Embodiment J is the method of any one of the preceding Embodiments, wherein the water-insoluble material comprises a water-insoluble material that sequesters a substance that interferes with a polymerase-mediated nucleic acid amplification reaction.

Embodiment K is the method of Embodiment J, wherein the water-insoluble material that sequesters a substance that interferes with a polymerase-mediated nucleic acid amplification reaction comprises a plurality of zirconium oxide particles, hydroxyapatite particles, or a mixture thereof.

Embodiment L is the method of Embodiment K, wherein the plurality of particles comprises a plurality of zirconium oxide particles having a mean particle size that is less than or equal to 100 nm.

Embodiment M is the method of Embodiment L, wherein the plurality of zirconium oxide particles has a surface area of about 10 $m^2$/L to about 600 $m^2$/L in the third volume.

Embodiment N is the method of any one of the preceding Embodiments, wherein subjecting the aqueous composition to a thermal lysis process comprises exposing the aqueous composition to a temperature of about 95° C. to about 102° C.

Embodiment O is the method of any one of the preceding Embodiments, wherein subjecting a portion of the aqueous composition to a nucleic acid amplification process comprises subjecting the portion of the aqueous composition to a loop-mediated isothermal amplification process.

Embodiment P is the method of any one of Embodiments A through N, wherein subjecting a portion of the aqueous composition to a nucleic acid amplification process comprises subjecting the portion of the aqueous composition to a thermocycling polymerase chain reaction process.

Embodiment Q is the method of any one of the preceding Embodiments, wherein forming the aqueous composition consists essentially of mixing the first volume of the enrichment culture with the second volume of the lysis buffer.

Embodiment R is the method of any one of the preceding claims, further comprising:

after subjecting the aqueous composition to the thermal lysis process and before subjecting the portion of the aqueous composition to the nucleic acid amplification process, rehydrating a dehydrated reagent for nucleic acid amplification using the portion of the aqueous composition.

Embodiment S is a lysis buffer, comprising:

a water-insoluble material that sequesters a substance that interferes with a polymerase-mediated nucleic acid amplification reaction;

an organic multivalent cation-chelating reagent;

at least one non-ionic surfactant;

ferric iron;

a reagent for facilitating polymerase activity;

a buffer; and water;

wherein the lysis buffer comprises less than 1 mM phosphoric acid or a salt thereof;

wherein the lysis buffer has a pH of about 9.8 to 10.5, inclusive, at 25° C.

Embodiment T is the lysis buffer of Embodiment S, wherein the buffer comprises N-cyclohexyl-3-aminopropanesulfonic acid or a salt thereof.

Embodiment U is the lysis buffer of Embodiment S or Embodiment T, wherein the water-insoluble material comprises a plurality of zirconium oxide particles, a plurality of hydroxyapatite particles, or a mixture thereof.

Embodiment V is the lysis buffer of Embodiment S or Embodiment T, wherein the organic multivalent cation-chelating reagent has an affinity constant greater than or equal to $10^{4.2}$ with respect to ferric iron ions and an affinity constant less than $10^{3.8}$ with respect to magnesium ions, wherein the first affinity constant and the second affinity constant are determined in 20° C. deionized water at pH 8.45.

Embodiment W is the lysis buffer of any one of Embodiments S through V, wherein the at least one non-ionic surfactant has a Hydrophilic-lipophilic balance of about 11 to about 16.

Embodiment X is the lysis buffer of any one of Embodiments S and U through W, wherein the buffer is selected from the group consisting of tris(hydroxymethyl)aminomethane, N-cyclohexyl-3-aminopropanesulfonic acid, 3-(N-morpholino)propanesulfonic acid, 4-(2-hydroxyethyl)-1-piperazineethanesulfonic acid, 2-[[1,3-dihydroxy-2-(hydroxymethyl)propan-2-yl]amino]ethanesulfonic acid, 2-[Bis(2-hydroxyethyl)amino]-2-(hydroxymethyl)propane-1,3-diol, and combinations thereof.

Embodiment Y is the lysis buffer of any one of Embodiments S through X, further comprising polyvinylpyrrolidone or polyvinylpolypyrrolidone.

Embodiment Z is the lysis buffer of any one of Embodiments S through Y, further comprising potassium chloride.

Embodiment AA is the lysis buffer of any one of Embodiments S through Z, further comprising ammonium sulfate.

Embodiment AB is the lysis buffer of any one of Embodiments S through AA, further comprising a reagent to facilitate nanoparticle dispersion.

Embodiment AC is the lysis buffer of any one of Embodiments S through AB, further comprising an indicator dye.

Embodiment AD is the lysis buffer of Embodiment AC, wherein the indicator dye is selected for monitoring a temperature of the lysis buffer.

Embodiment AE is the lysis buffer of any one of Embodiments S through AD, wherein the lysis buffer has a pH of about 10.0 to 10.2, inclusive, at 25° C.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Materials and Reagents.

A zirconium oxide nanoparticle dispersion (10% w/w in water; <100 nm particle size (BET); Part No. 643025) was obtained from Sigma Chemical Co. TRITON™ X-100 detergent and Proclin® 950 biocide were obtained from Sigma-Aldrich (St. Louis, Mo.). The test compositions were prepared with each component added to deionized water in the order specified in Table 1.

TABLE 1

Lysis buffer. Composition of Lysis buffer used in the Examples. The order of addition of each component of the composition is also shown.

| Order of Addition to Water | Component | Concentration |
|---|---|---|
| 1 | Ferric ammonium citrate | 657 mg/L |
| 2 | Potassium Citrate | 972 mg/L |
| 3 | TRITON ™ X-100 detergent | 10 g/L |
| 4 | PVP | 4.3 g/L |
| 5 | Zirconium oxide dispersion (10% w/w) | 20 mL/L |
| 6 | Cresol Red | 100 mg/L |
| 7 | Magnesium sulfate heptahydrate | 738 mg/L |
| 8 | N-cyclohexyl-3-aminopropanesulfonic acid | 22.1 g/L |
| 9 | Potassium Hydroxide | 100 mM |
| 10 | Ammonium Hydroxide | 14.1 g/L |
| 11 | EGTA | 4.75 g/L |
| 12 | Proclin ® 950 biocide | 5.26 mL/L |

TABLE 2

Enrichment Medium. Composition of the enrichment medium used in the Examples.

| Component | Concentration |
|---|---|
| Tris HCl | 3.51 g/L |
| Tris Base | 0.34 g/L |
| Potassium Chloride | 3 g/L |
| Glucose | 5 g/L |
| Yeast Extract | 5 g/L |
| Peptone | 10 g/L |

TABLE 3

Alternative Lysis Buffer used for Comparative Examples. The concentration of each component were adjusted so that, when mixed with the sample according to the conventional method, each component was at the proper final concentration for the nucleic acid amplification step.

| Order of Addition to Water | Component | Concentration |
|---|---|---|
| 1 | Ferric ammonium citrate | 200 mg/L |
| 2 | TRITON ™ X-100 detergent | 320 mg/L |
| 3 | PVP | 430 mg/L |
| 4 | Zirconium oxide dispersion (10% w/w) | 2 mL/L |
| 5 | Cresol Red | 10 mg/L |
| 6 | Magnesium sulfate heptahydrate | 73.8 mg/L |
| 7 | Potassium chloride | 3.19 g/L |
| 8 | Tris base | 2.72 g/L |
| 9 | Ammonium sulfate | 1.41 g/L |
| 10 | EGTA | 475 mg/L |
| 11 | Proclin ® 950 biocide | 0.526 mL/L |

Example 1

Detection of *Salmonella* Microorganisms Using Non-Dilutive Sample-Preparation Method Overnight cultures of *E. coli* (ATCC 25922) and *Salmonella* (ATCC 6962), respectively, were grown by picking an isolated colony of each microorganisms from a blood agar plate, suspending the colonies in separate tubes containing 10 mL of the enrichment medium described in Table 2, and incubating each of the tubes for 18 hours at 37° C. After the incubation period, the *Salmonella* culture was enumerated and serially diluted into the *E. coli* culture to obtain mixed cultures having about $5 \times 10^9$ CFU/mL of *E. coli* mixed with a *Salmonella* subpopulation of about $5\times10^6$ CFU/mL *Salmonella*, about $5\times10^5$ CFU/mL *Salmonella*, about $5\times10^4$ CFU/mL *Salmonella*, about $5\times10^3$ CFU/mL *Salmonella*, about $5\times10^2$ CFU/mL *Salmonella*, about $5\times10^1$ CFU/mL *Salmonella*, about $5\times10^0$ CFU/mL *Salmonella*, and about $5\times10^{-1}$ CFU/mL *Salmonella* in the respective tubes.

55 µL aliquots of the lysis buffer (Table 1) were pipetted into lysis tubes (Axygen Minitube 1.1 mL Fisher cat #: 14-222-202). To each individual lysis tube, 500 µL of one of each of the mixed cultures of *E. coli* and *Salmonella* (described above) was added. The lysis tubes were then processed by placing them in contact with a heat block set to 100° C. for 15 minutes. The tubes were then cooled for 5 minutes by placing them in contact with a room temperature metal block for 5 minutes.

After the thermal lysis and cooling steps, five 20 µL aliquots of the lysate were removed from each lysis tube and each aliquot was used to reconstitute a 3M MDS *Salmonella* reagent pellet (cat #: MDA2SAL96; 3M Company; St. Paul, Minn.) in individual reaction tubes. Thus, approximately 100 µL of lysate (approximately 90 µL of the mixed culture) from each lysis tube was analyzed for the presence of *Salmonella* microorganisms. The reaction tubes were placed into a 3M Molecular Detection System instrument (cat # MDS100; 3M Company; St. Paul, Minn.) and the instrument was operated according to the manufacturer's instructions in order to detect amplification of *Salmonella* DNA. The results are reported in Table 4.

Comparative Example 1

Detection of *Salmonella* Microorganisms Using Conventional Method

Each of the mixed cultures of *E. coli* and *Salmonella* prepared in Example 1 was tested using the conventional method (described in the manufacturer's instructions) of detecting *Salmonella* microorganisms with a 3M Molecular Detection System kit (cat #: MDA2SAL96). Briefly, 20 µL of each sample were added to individual lysis tubes containing 580 µL of alternative lysis buffer (Table 3). The lysis tubes then were heated for 15 minutes and cooled for 5 minutes as described in Example 1.

After the thermal lysis and cooling steps, five 20 µL aliquots of the lysate were removed from each lysis tube and each aliquot was used to reconstitute a 3M MDS *Salmonella* reagent pellet (cat #: MDA2SAL96; 3M Company; St. Paul, Minn.) in individual reaction tubes. Thus, approximately 100 µL of lysate (approximately 3 µL of the mixed culture) from each lysis tube was analyzed for the presence of *Salmonella* microorganisms. The reaction tubes were placed into a 3M Molecular Detection System instrument (cat # MDS100; 3M Company; St. Paul, Minn.) and the instrument was operated according to the manufacturer's instructions in order to detect amplification of *Salmonella* DNA. The results are reported in Table 4.

TABLE 4

Amplification of *Salmonella* DNA from mixed cultures of *E. coli* and *Salmonella*. A negative ("−") result indicates none of the five reaction tubes showed amplification of *Salmonella* microorganism DNA. A positive ("+") result indicates at least one of the five reaction tubes showed amplification of *Salmonella* microorganism DNA.

| *Salmonella* Level (CFU/mL) | Comparative Example 1 | Example 1 |
|---|---|---|
| $5 \times 10^6$ | + | + |
| $5 \times 10^5$ | + | + |
| $5 \times 10^4$ | + | + |

TABLE 4-continued

Amplification of *Salmonella* DNA from mixed cultures of *E. coli* and *Salmonella*. A negative ("−") result indicates none of the five reaction tubes showed amplification of *Salmonella* microorganism DNA. A positive ("+") result indicates at least one of the five reaction tubes showed amplification of *Salmonella* microorganism DNA.

| *Salmonella* Level (CFU/mL) | Comparative Example 1 | Example 1 |
|---|---|---|
| $5 \times 10^3$ | − | + |
| $5 \times 10^2$ | − | + |
| $5 \times 10^1$ | − | + |
| $5 \times 10^0$ | − | − |
| $5 \times 10^{-1}$ | − | − |

Example 2

Detection of *Campylobacter* Microorganisms Using Non-Dilutive Sample-Preparation Method Overnight cultures of *E. coli* (ATCC 25932) and *Campylobacter jejuni* (ATCC 33291), respectively, were grown by picking an isolated colony of each microorganisms from a blood agar plate, suspending the colonies in separate tubes containing 10 mL of the enrichment medium described in Table 2, and incubating each of the tubes for 18 hours at 37° C. (*E. coli*) or 41.5° C. (*C. jejuni*), respectively. After the incubation period, the *Campylobacter* culture was enumerated and serially diluted into the *E. coli* culture to obtain mixed cultures having about $5\times10^9$ CFU/mL of *E. coli* mixed with a *Campylobacter* subpopulation of about $5\times10^6$ CFU/mL *Campylobacter*, about $5\times10^5$ CFU/mL *Campylobacter*, about $5\times10^4$ CFU/mL *Campylobacter*, about $5\times10^3$ CFU/mL *Campylobacter*, about $5\times10^2$ CFU/mL *Campylobacter*, about $5\times10^1$ CFU/mL *Campylobacter*, about $5\times10^0$ CFU/mL *Campylobacter*, and about $5\times10^{-1}$ CFU/mL *Campylobacter* in the respective tubes.

Aliquots (500 µL) of each mixed culture of *E. coli* and *Campylobacter* was lysed as described in Example 1. To individual reaction tubes, five microliter aliquots of each lysate were added to a qPCR master mixture consisting of PCR buffer and each of the following components: 0.2 mM dNTP's, 3 mM MgCl2, 2.5 U of Taq DNA polymerase, 0.625 µM forward primer [SEQ ID NO: 1 (CTGCT-TAACACAAGTTGAGTAGG)], 0.625 µM reverse primer [SEQ ID NO: 2 (TTCCTTAGGTACCGTCAGAA)], Brilliant III Master Mix (Part Number 600880, Agilent Technologies), and 0.156 µM *Campylobacter* probe [SEQ ID NO: 3 (FAM-TGTCATCCTCCACGCGGCGTTGCTGC-TAMRA)]. Each of the aforementioned concentrations is reported as the concentration in the mixture after addition of the lysate (i.e., the "final" concentration). Each reaction tube was processed in an Applied Biosystems 7500 thermal cycler.

Thermocycling reactions were run for 40 cycles using the following protocol: (1) denature (95° C. for 30 seconds), (2) anneal (58° C. for 30 seconds), and (3) extend (72° C. for 60 seconds).

Comparative Example 2

Detection of *Campylobacter* Microorganisms Using Conventional Method

Each of the mixed cultures of *E. coli* and *Campylobacter* prepared in Example 1 was tested using a conventional PCR method. To prepare the lysate for the PCR reaction 20 μL of each sample were added to individual lysis tubes containing 580 μL of lysis buffer from a 3M Molecular Detection System kit (cat #: MDA2SAL96). The lysis tubes then were heated for 15 minutes and cooled for 5 minutes as described in Example 1.

Five microliter aliquots of each lysate was subjected to DNA amplification as described in Example 2.

TABLE 5

Semi-quantitative detection results for the thermocycling *Campylobacter*-amplification reactions. Results are shown as the number of positive PCR reactions (i.e., in which *Campylobacter* DNA was detected) over the number of total PCR reactions tested.

| *Campylobacter* Level (CFU/mL) | Example 2 | Comparative Example 2 |
|---|---|---|
| $5 \times 10^7$ | 3/3 | 3/3 |
| $5 \times 10^6$ | 3/3 | 3/3 |
| $5 \times 10^5$ | 3/3 | 3/3 |
| $5 \times 10^4$ | 3/3 | 3/3 |
| $5 \times 10^3$ | 3/3 | 2/3 |
| $5 \times 10^2$ | 3/3 | 2/3 |
| $5 \times 10^1$ | 3/3 | 1/3 |
| $5 \times 10^0$ | 2/3 | 0/3 |

The data show that a method of the present disclosure (e.g., as performed in Example 2) can reliably detect a lower concentration of microorganisms in a sample than the conventional methods (e.g., Comparative Example 2).

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

What is claimed is:

1. A nucleic acid amplification method, said method comprising:
    forming an enrichment culture by contacting a sample with a nutrient medium having a formulation that does not include a phosphate buffer component, wherein the nutrient medium comprises a first buffer;
    holding the enrichment culture for a period of time at a temperature that facilitates growth of a target microorganism;
    after holding the enrichment culture, forming an aqueous composition by mixing a first volume of the enrichment culture with a second volume of a lysis buffer to form a third volume of the aqueous composition;
    wherein mixing the first volume of the enrichment culture with the second volume of the lysis buffer comprises mixing an undiluted first volume of the enrichment culture with the second volume of the lysis buffer;
    wherein the lysis buffer comprises a second buffer;
    wherein the lysis buffer comprises an organic multivalent cation-chelating reagent, wherein the organic multivalent cation-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45;
    wherein the lysis buffer has a pH greater than 8.6 at 25° C.;
    wherein the aqueous composition has a pH of about 8.45 to 8.85 at 25° C.;
    wherein a combined concentration of the first buffer and the second buffer in the aqueous composition is at least about 15 mM;
    wherein the ratio of the first volume to the second volume is greater than or equal to 3:1 and the ratio of the second volume to the third volume is less than or equal to 1:4;
    contacting the aqueous composition with an effective amount of a water-insoluble material that sequesters a substance that interferes with a polymerase-mediated nucleic acid amplification reaction;
    subjecting the aqueous composition to a thermal lysis process; and
    after subjecting the aqueous composition to the thermal lysis process, subjecting a portion of the aqueous composition to an isothermal nucleic acid amplification process.

2. The method of claim 1, wherein the lysis buffer further comprises ferric iron.

3. The method of claim 1, wherein the lysis buffer further comprises a reagent selected from the group consisting of a nanoparticle dispersion stabilizer, a non-ionic surfactant having a hydrophilic-lipophilic balance of about 11 to about 16, polyvinylpyrrolidone, magnesium sulfate heptahydrate, a fluorosurfactant, an indicator dye, and a combination of any two or more of the foregoing reagents.

4. The method of claim 1, wherein holding the enrichment culture for a period of time comprises holding the enrichment culture for a period of about 4 hours to about 24 hours.

5. The method of claim 1, wherein the ratio of the first volume to the second volume is greater than or equal to 5:1 and the ratio of the second volume to the third volume is less than or equal to 1:6.

6. The method of claim 1, wherein forming the aqueous composition by mixing the first volume of the enrichment culture with the second volume of the lysis buffer comprises forming the aqueous composition with the water-insoluble material that sequesters out of the aqueous composition a substance that interferes with a polymerase-mediated nucleic acid amplification reaction disposed therein.

7. The method of claim 1, wherein the water-insoluble material comprises a plurality of zirconium oxide particles.

8. The method of claim 7, wherein the plurality of zirconium oxide particles has a surface area of about 10 $m^2/L$ to about 600 $m^2/L$ in the third volume.

9. The method of claim 1, wherein subjecting a portion of the aqueous composition to a nucleic acid amplification process comprises subjecting the portion of the aqueous composition to a loop-mediated isothermal amplification process.

10. The method of claim 1, wherein forming the aqueous composition consists essentially of mixing the first volume of the enrichment culture with the second volume of the lysis buffer.

11. The method of claim 1 further comprising:
    after subjecting the aqueous composition to the thermal lysis process and before subjecting the portion of the aqueous composition to the nucleic acid amplification process, rehydrating a dehydrated reagent for nucleic acid amplification using the portion of the aqueous composition.

12. The method of claim 1, wherein the enrichment culture comprises peptone.

* * * * *

SEQUENCE LISTING

<160> NUMBER OF SEQ ID NOS: 3

<210> SEQ ID NO 1
<211> LENGTH: 23
<212> TYPE: DNA
<213> ORGANISM: Campylobacter spp.

<400> SEQUENCE: 1
ctgcttaaca caagttgagt agg                                      23

<210> SEQ ID NO 2
<211> LENGTH: 20
<212> TYPE: DNA
<213> ORGANISM: Campylobacter spp.

<400> SEQUENCE: 2
ttccttaggt accgtcagaa                                          20

<210> SEQ ID NO 3
<211> LENGTH: 26
<212> TYPE: DNA
<213> ORGANISM: Campylobacter spp.

<400> SEQUENCE: 3
tgtcatcctc cacgcggcgt tgctgc                                   26